(12) United States Patent
Huang

(10) Patent No.: US 11,738,110 B2
(45) Date of Patent: Aug. 29, 2023

(54) MAGNETICALLY ATTACHABLE UV LED SANITIZER SYSTEM

(71) Applicant: Zhenwu Huang, Las Vegas, NV (US)

(72) Inventor: Zhenwu Huang, Las Vegas, NV (US)

( * ) Notice: Subject to any disclaimer, the term of this patent is extended or adjusted under 35 U.S.C. 154(b) by 422 days.

(21) Appl. No.: 16/996,901

(22) Filed: Aug. 19, 2020

(65) Prior Publication Data

US 2022/0054696 A1      Feb. 24, 2022

(51) Int. Cl.
*A61L 9/20*        (2006.01)
*G01P 13/00*       (2006.01)

(52) U.S. Cl.
CPC .............. *A61L 9/20* (2013.01); *G01P 13/00* (2013.01); *A61L 2209/11* (2013.01); *A61L 2209/12* (2013.01); *A61L 2209/16* (2013.01)

(58) Field of Classification Search
CPC .... A61L 9/20; A61L 2209/11; A61L 2209/12; A61L 2209/16; A61L 9/00; G01P 13/00; F21V 21/096; F21V 21/0965
See application file for complete search history.

(56) References Cited

U.S. PATENT DOCUMENTS

2017/0000916 A1 *    1/2017   Stibich .................... A61L 2/14

* cited by examiner

*Primary Examiner* — Bao Q Truong
(74) *Attorney, Agent, or Firm* — The Thornton Firm, LLC

(57) ABSTRACT

A magnetically attachable UV LED sanitizer system for indoor spaces having an outer shell assembly consisting of a rectangular cuboid outer machine shell, a front plate, and a back plate shaped in such a manner so as to fit inside an air conditioning duct register, diffuser or grille; a transparent cover, said cover allowing for the transmission of germicidal ultraviolet light frequencies; an ultraviolet lamp board; a motion detector capable of detecting movement of persons in an indoor space; at least one processor; a power supply; a rechargeable battery; a wireless network card; a magnet assembly capable of adhering the system to ferromagnetic surfaces such as air conditioning ducts, registers, diffusers and grilles. The system is programmable to emit germicidal ultraviolet radiation to sanitize air traveling to, from and through air conditioning ducts. The device is networkable with devices such as computers, smartphones and tablets.

18 Claims, 6 Drawing Sheets

MAGNETICALLY ATTACHABLE UV LED SANITIZER SYSTEM

CROSS-REFERENCE TO RELATED APPLICATIONS

Not applicable.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

1. Field of the Invention

The invention relates generally to the field of air sanitizers which employ ultraviolet radiation. More specifically, the present invention relates to a magnetically attachable and networkable ultraviolet sanitizing device for sanitizing air in indoor spaces.

2. Description of the Related Art

The world has an increased awareness of infectious disease and is currently searching for ways to combat the spread of pathogenic bacteria and viruses. Due to the COVID-19 pandemic, improved sanitizing devices are not only desired, they have become a necessary element in both living and work spaces.

It is now a well-known fact that COVID-19 is transmitted by human-to-human contact and is considered to be a highly infectious disease. One of the predominant mechanisms for pathogenic agents to be contagious is self-inoculation from contaminated surfaces. Self-inoculation could occur by poor hand hygiene or by not following common disease-controlling etiquettes such as frequent hand to face contact.

In addition to transmission though contact with contaminated surfaces, respiratory particles, whether they be droplets or aerosols based on the particle size and specifically in terms of the aerodynamic diameter, are a well-known and understood means of disease transmission. It has been proven that viral disease outbreaks via aerosol transmission is a serious concern as droplets and aerosols containing bacterial and viral pathogens may remain airborne for enough time to infect susceptible people.

Air conditioning ducts pose themselves as a particular hazard when it comes to the spread of infectious disease through pathogens in droplets or aerosols. Because droplets and aerosols may remain airborne for a considerable amount of time, they may be spread throughout a building in a short amount of time. In addition to droplets and aerosols spread by coughing and sneezing, certain pathogens may be able to live and survive inside of air conditioning systems. Moreover, pathogens such as viruses and other bacteria may be spread to other spaces in a building through such ducts.

Germicidal techniques and air sanitizers are known in the art. Numerous methods inventions have been created and implemented to clean and sanitize both surfaces and the surrounding air. Among the most popular methods of sanitizing both surfaces and the surrounding air is the use of chemical sanitizers.

Chemical sanitizers for air involve the introduction of an aerosolized chemical mixture into the air. Though this method of disinfecting air has proven effective, many chemical sanitizers can irritate respiratory and integumentary systems.

As an alternative to chemical sanitizers, the use of ultraviolet irradiation devices has become widely used. Ultraviolet sanitizing devices essentially consist of a device where ultraviolet lights irradiate surfaces and the surrounding space. Such ultraviolet irradiation has proven itself highly effective in killing pathogens, and several portable devices have been created. However, irradiation of ambient air in indoor spaces has still proven problematic due to the size of current sanitizers and the lack of protection caused air movement caused by air conditioning ducts.

Presently, there exists a need for an improved, low maintenance, magnetic UV LED air sanitizing system and method for sanitizing air in indoor spaces. Such a system must be able to effectively replace chemical sanitizers. Additionally, such as system must be able to insure that such a system is optimized to current health and safety standards. Furthermore, such a system should produce an increased amount of sanitized air while providing an easy-to-use system which may be networkable with other internet enabled devices.

SUMMARY

The present invention is directed to an improved UV LED air sanitizing system and method for sanitizing air in indoor spaces. Such a system can effectively replace the use of chemical sanitizers in indoor air spaces. Use of the magnetically attachable UV LED sanitizer is conducive to an institution's compliance with current health and safety standards. Moreover, the magnetically attachable UV LED sanitizer system is capable of producing an increased amount of sanitized air while providing an easy-to-use system which may be networkable with other internet enabled devices.

An object of the present invention is to provide an improved UV sanitizing system which can be specifically configured to sanitize air entering, travelling through, and exiting existing heating, cooling and air conditioning ductwork. The invention is shaped and configured to magnetically attach to air conditioning vents and ducts providing a user a portable, but reliable air sanitizing system which can be used for spaces such as offices, homes, hotel rooms, hospital rooms, and other indoor spaces where sanitized air is desired. The magnetically attachable UV LED air sanitizing system model is equipped with a rechargeable lithium battery. The system uses at least one magnet for attaching to ferromagnetic surfaces such as, but not limited to, air conditioning ducts, vents, registers and grilles.

The magnetically attachable UV LED sanitizer system consists of one or more UV LED sanitizer system units, each unit comprising an outer shell assembly consisting of a rectangular cuboid outer machine shell, a front plate, and a back plate shaped in such a manner so as to fit inside an air conditioning duct register, diffuser or grille; a transparent cover, said cover allowing for the transmission of germicidal ultraviolet light frequencies; an ultraviolet lamp board; a motion detector capable of detecting movement of persons in an indoor space which, upon detection of motion, sends an electric signal to the at least one processor which can turn the ultraviolet lamp board; at least one processor; a power supply; a rechargeable battery; a wireless network card; a magnet assembly, said magnet assembly positioned on the opposite side of the transparent cover so as to attach to ferromagnetic surfaces such as air conditioning ducts, registers, diffusers and grilles; and memory storing computer readable instructions that, when executed by the at least one processor, cause the magnetically attachable UV LED sanitizer system to irradiate a space with germicidal UV radiation from the said ultraviolet lamp board.

Compared with other UV LED light sanitizer products, the present invention not only inhibits the growth of pathogens such as bacteria and viruses, but also can be conveniently attached to metal surfaces such as a central air-conditioning tube. As a method of operation, the UV disinfection can be carried out remotely and at regular intervals through wireless networks. In some embodiments, a motion sensor detects human body movements so as to activate the UV LED sanitizing system to protect the person when she or he enters a room. The magnetically attachable UV LED sanitizer system is easy to install and disassemble. The magnetically attachable UV LED sanitizer system is also convenient for intelligent control to adapt to user needs which allows for a healthier living environment.

A further object of the invention is to provide a system which is capable of sanitizing a greater amount of air than existing UV LED sanitizer systems. The present invention is designed to attach to heating, ventilation and air conditioning (HVAC) ducts so as to create a system which sanitizes air moving into, through or from HVAC systems. Moreover, the invention uses a light emitting diode board which is capable of emitting a greater amount of germicidal UV radiation as well as a lamp board which is capable of withstanding higher operating temperatures. The present invention can be used for household epidemic prevention, sterilization, and inhibition of viruses and bacteria. It can be effectively used in shopping malls, office buildings, stations, airports and other public places having typical air conditioning systems.

BRIEF DESCRIPTION OF THE DRAWINGS

The invention directed by way of example, and not by way of limitation, in the figures of the accompanying drawings and in which like reference numerals refer to similar elements and in which.

Figure 1:
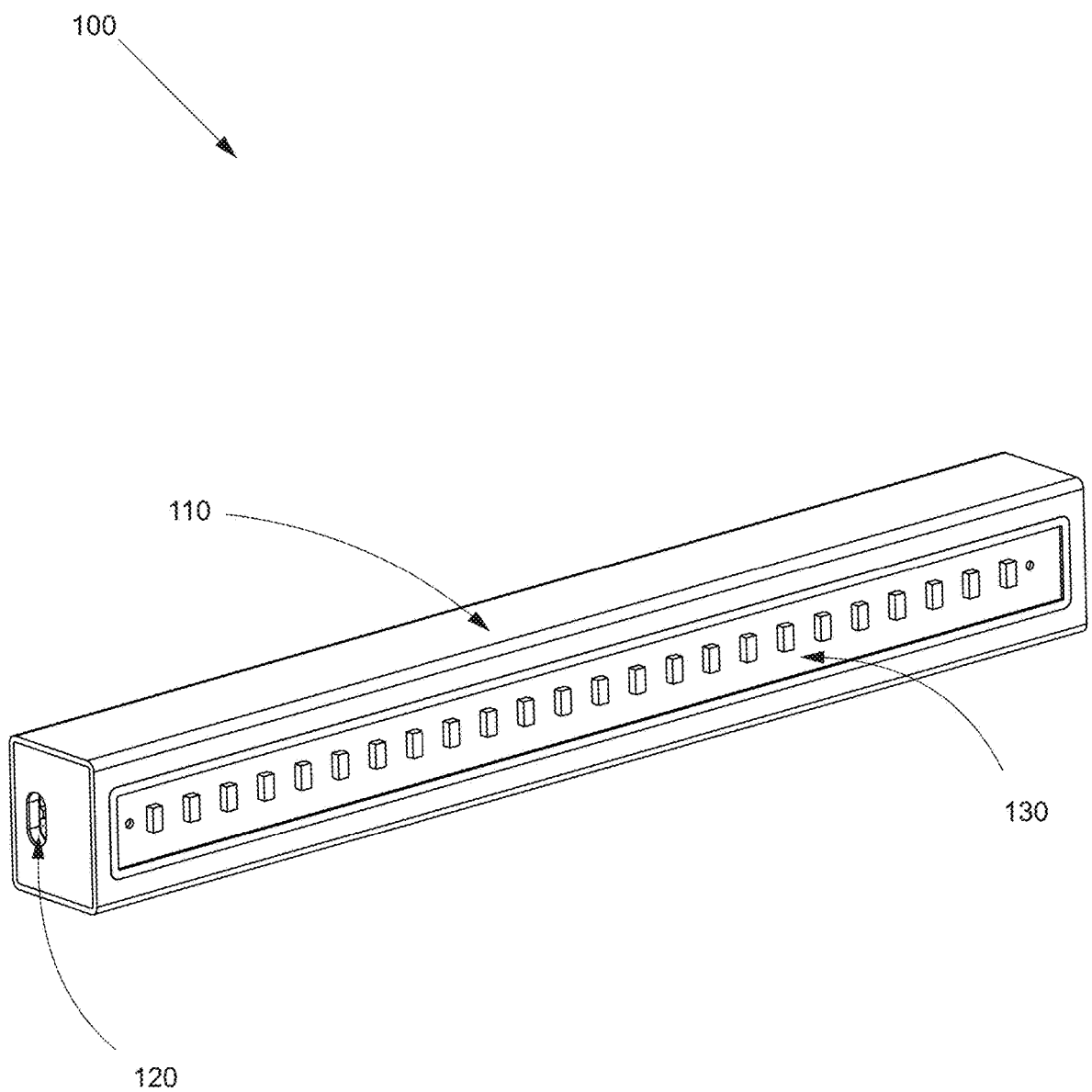
FIG. 1 is a perspective illustration of an exemplary magnetically attachable UV LED sanitizer in accordance with an embodiment of the invention.

Unless otherwise indicated illustrations in the figures are not necessarily drawn to scale.

DETAILED DESCRIPTION OF THE PREFERRED EMBODIMENTS

Terminology used herein is used for the purpose of describing particular embodiments only, and is not intended to limit the scope of the present invention. It must be understood that as used herein and in the appended claims, the singular forms "a," "an," and "the" include the plural reference unless the context clearly dictates otherwise. For example, a reference to "an element" is a reference to one or more elements and includes all equivalents known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Language that may be construed to express approximation should be so understood unless the context clearly dictates otherwise.

Unless defined otherwise, all technical and scientific terms used herein have the same meanings as commonly understood by a person of ordinary skill in the art to which this invention belongs. Preferred methods, techniques, devices, and materials are described. But any methods, techniques, devices, or materials similar or equivalent to those described herein may be used in the practice or testing of the present invention. Structures described herein should also be understood to refer to functional equivalents of such structures.

References to "one embodiment," "one variant," "an embodiment," "a variant," "various embodiments," "numerous variants," etc., may indicate that the embodiment(s) of the invention so described may include particular features, structures, or characteristics. However, not every embodiment or variant necessarily includes the particular features, structures, or characteristics. Further, repeated use of the phrase "in one embodiment," or "in an exemplary embodiment," or "a variant," or "another variant," do not necessarily refer to the same embodiment although they may. A description of an embodiment with several components in communication with each other does not imply that all such components are required. On the contrary, a variety of optional components are described to illustrate the wide variety of possible embodiments and/or variants of the present invention.

"Sanitizer" refers to a substance or device for killing or reducing levels of pathogenic microorganisms to safe levels.

"Ultraviolet germicidal irradiation" or "UVGI" is a germicidal technique where ultraviolet radiation is used to kill or inactivate microorganisms. Ultraviolet radiation is mutagenic to bacteria, viruses and other microorganisms, with short-wavelength ultraviolet radiation considered to be "germicidal" at wavelengths between 100-280 nanometers.

A "computer" may refer to one or more apparatus and/or one or more systems that are capable of accepting a structured input, processing the structured input according to prescribed rules, and producing results of the processing as output. Examples of a computer may include: a personal computer (PC); a stationary and/or portable computer; a computer having a single processor, a computer having multiple processors, or a computer having multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer; a personal digital assistant (PDA); a portable telephone; a portable smartphone; wearable devices such as smartwatches; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

The term "processor" may refer to any device or portion of a device that processes electronic data from registers and/or memory to transform that electronic data into other electronic data that may be stored in registers and/or memory. A "computing platform" may comprise one or more processors.

A "microcontroller" or "microcontroller unit" generally refers a small computer on a single integrated circuit. A microcontroller contains one or more central processing units (processor cores) along with memory and programmable input/output peripherals. A typical microcontroller includes a processor, memory and input/output (I/O) peripherals on a single chip.

An "algorithm" is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

It will be readily understood by persons skilled in the art that the various methods and algorithms described herein may be implemented by appropriately programmed computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

"Software" may refer to prescribed rules and/or instructions used to operate a computer. Examples of software may include: code segments in one or more computer-readable languages; graphical and or/textual instructions; applets; pre-compiled code; interpreted code; compiled code; and computer programs. An operating system or "OS" is software that manages computer hardware and software resources and provides common services for computer programs.

Certain embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages or other compilers, assemblers, interpreters or other computer languages or platforms.

A "computer system" may refer to a system having one or more computers, where each computer may include a computer-readable medium employing software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" generally refers to a plurality of computers and associated devices that may be connected by various communication channels to facilitate communication and resource sharing. A network may involve permanent connections such as cables or temporary connections such as those made through telephone, cable, wireless or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include, but are not limited to, an internet, such as the Internet or World Wide Web; an intranet; a personal area network (PAN); near field communication (NFC); a local area network (LAN); a wide area network (WAN); a virtual private network (VPN); internet of things (IoT); and a combination of networks, such as an internet and an intranet.

Exemplary networks may operate with any of a number of protocols such as, but not limited to, Transmission Control Protocol (TCP), Internet protocol (IP), Internet Address Protocol (IP Address), asynchronous transfer mode (ATM), Near Field Communication digital protocol, and/or synchronous optical network (SONET), user datagram protocol (UDP), IEEE 802.x, etc.

As is well known to those skilled in the art, many careful considerations and compromises typically must be made when designing the optimal manufacture or commercial implementation of such a magnetically attachable UV LED sanitizer. A commercial implementation in accordance with the spirit and teachings of the invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art.

The exemplary magnetically attachable UV LED sanitizer will now be described in detail with reference to embodiments thereof as illustrated in the accompanying drawings. Unless otherwise indicated illustrations in the figures are not necessarily drawn to scale.

FIG. 1 is a perspective illustration of an exemplary magnetically attachable UV LED sanitizer in accordance with an embodiment of the invention. At its essence, the magnetically attachable UV LED sanitizer system comprises a power supply 110, an outer shell 120 and an LED lamp board 130. In the preferred embodiment of the invention, the power supply consists of a 12-volt rechargeable lithium ion battery system. Persons having skill in the art will understand that such a battery system is rechargeable through numerous AC power supplies. The lithium-ion battery system may consist of one or more rechargeable cells, preferably with a high capacity rating. In embodiments of the invention, the power supply 110 may consist of a 110 volt or 220 volt external supply known and appreciated in the art. Persons skilled in the art will readily appreciate that numerous power supply options are available to charge batteries and power the device in locations where power supply parameters such as voltage may vary. In alternative embodiments, the power supply may come from a Universal Serial Bus (USB) cable which is networkable with numerous electronic devices understood in the art.

Figure 2:
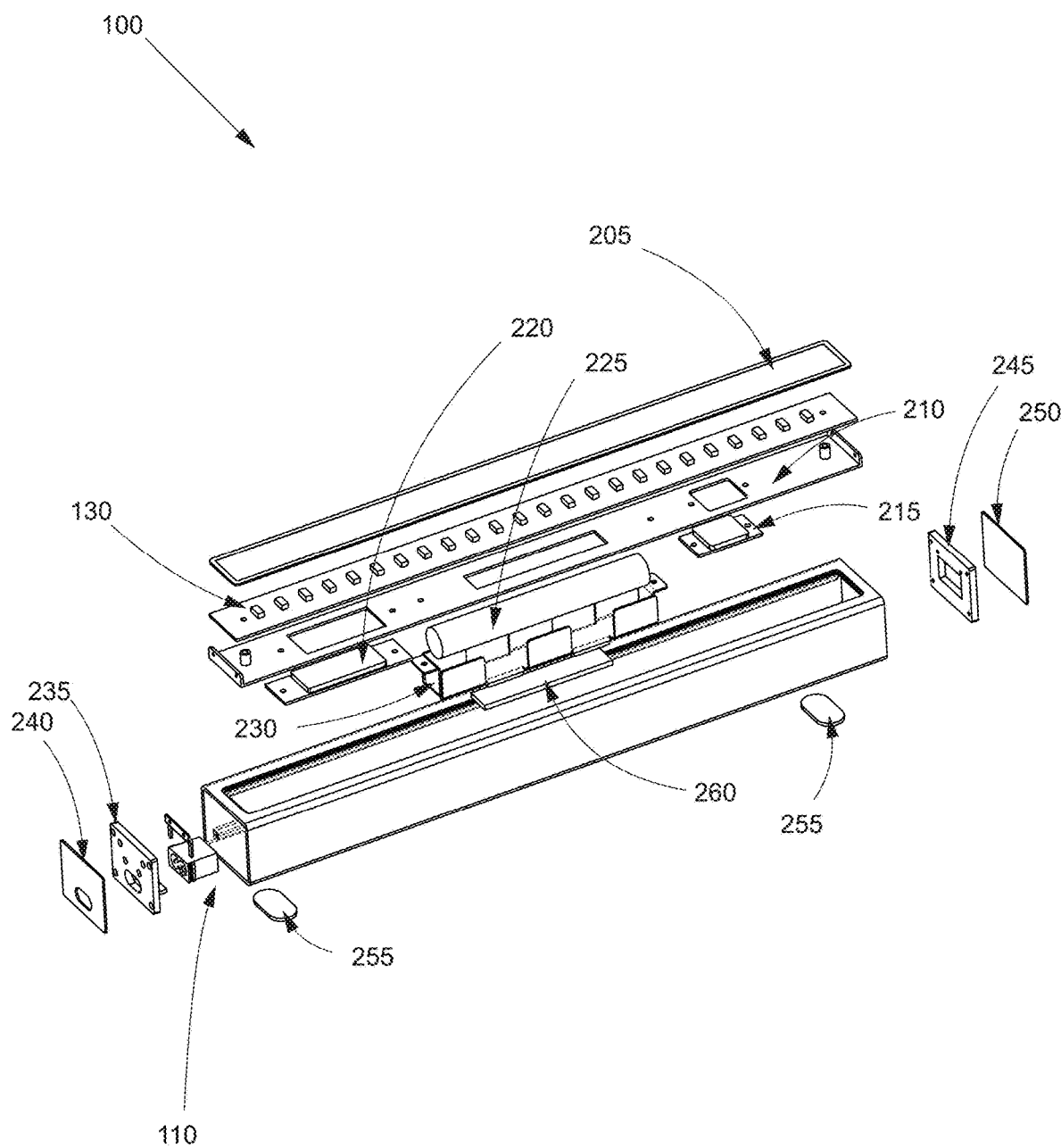
FIG. 2 is an exploded perspective view of a magnetically attachable UV LED sanitizer in accordance with an embodiment of the invention.

The outer shell 120 is made of a rigid metal alloy material such as, but not limited to, polished aluminum alloy. Alternatively, the outer shell may be made from an ABS plastic material configured to fix and protect the internal accessories. Persons having skill in the art will understand that numerous materials may be used to create an outer shell. It will be understood by persons having skill in the art that the primary objects of the outer shell are to provide for protection of the inner components and to create an object shape which is conducive for fitting inside air conditioning vents, ducts, The LED lamp board 130 consists of a plurality of ultraviolet light emitting diodes (LEDs). In one embodiment, the LED lamp board contains 24 UV emitting LEDs. However, the number of LEDs can vary depending on factors such as unit size and ultraviolet germicidal radiation demand FIG. 2 is an exploded perspective view of a magnetically attachable UV LED sanitizer in accordance with an embodiment of the invention. In addition to a power supply 110, an outer shell 120 and an LED lamp board 130, the invention further comprises a quartz glass cover board 205, a motherboard bracket 210, a motion detector controller board 215, a microprocessor board with wireless networking board 220, a battery 225, a battery bracket 230, a front plate plug 235, a front patch 240, a back plate plug 245, a back patch 250, one or more shell silicone pads 255, and one or more magnets 260 capable of attaching to ferromagnetic surfaces.

The LED ultraviolet lamp board has a transparent cover 205 superior to or in front of the LED lamp board for encapsulation and protection. The transparent cover allows for the transmission of germicidal ultraviolet radiation. In embodiments of the invention, the transparent cover can be made any suitable material ranging from quartz glass to a transparent plastic. The object of the transparent cover is to protect the LED lamp board while allowing a maximum amount of germicidal radiation to pass through.

The microprocessor board with wireless networking board 220 includes at least one processor and is held in place by a motherboard bracket 210. In embodiments of the invention, the at least one processor is a microcontroller unit (MCU) capable of performing programmable instructions that is known and appreciated in the art. The microprocessor board with wireless networking board allows for networking with mobile devices such as, but not limited to, smartphones and tablets. By way of example, and not limitation, a user may access a software application on a mobile device which is capable of transmitting signals to the MCU which controls the operation of the LED lamp board 130. It is to be understood that the microprocessor board includes memory storing computer readable instructions that, when executed by the at least one processor, cause the magnetically attachable UV LED sanitizer system to irradiate a space with germicidal UV radiation from the said ultraviolet lamp board.

A motion detector controller board 215 is also included in the invention. Persons having skill in the art will understand that a motion controller board is governed by a sensor which detects motion in a given space. In the present invention, a person need only enter a room for the motion detector to activate the LED lamp board or send a signal to a networked device via a microprocessor board wireless networking board 220 and receive instructions by the same network. When a moving object approaches the magnetically attachable UV LED sanitizer unit within a general radius of 2-3 meters, the sensor sends the signal to the main board processor. After the at least one processor on the microprocessor board with wireless networking board 220 receives a signal from sensor, an red indicator light will be on. At this time, the at least one processor will send a signal to a timer, which will temporarily turn off the UV light for 8-10 seconds. After 8-10 seconds, if there are moving objects near the product, it will continue to be off and waiting for the next 8-10 seconds. If the sensor does not detect a moving object within 8-10 seconds, the motion sensor will send a signal to the microprocessor board wireless networking board 220, and the product will return to its previous working state.

In the preferred embodiment of the invention, the LED lamp board 130 is formed through aluminum substrate processing. Such aluminum substrate processing provides for improved heat dissipation. In embodiments of the invention, the LED core material is a flat-type indium gallium nitride (InGaN) light emitting diode. Novel flat-type indium gallium nitride (InGaN) LEDs are capable of emitting radiation at greater intensities for greater distances. Persons having skill in the art will appreciate that other suitable materials known and appreciated in the art may be used. In the preferred embodiment of the invention, the LEDs produce germicidal UV radiation at a wavelength between 270 and 280 nanometers. For embodiments of the invention, the effective germicidal radiation distance is 50 centimeters with an irradiation angle from the LED lamp board being 120 degrees.

Figure 3:
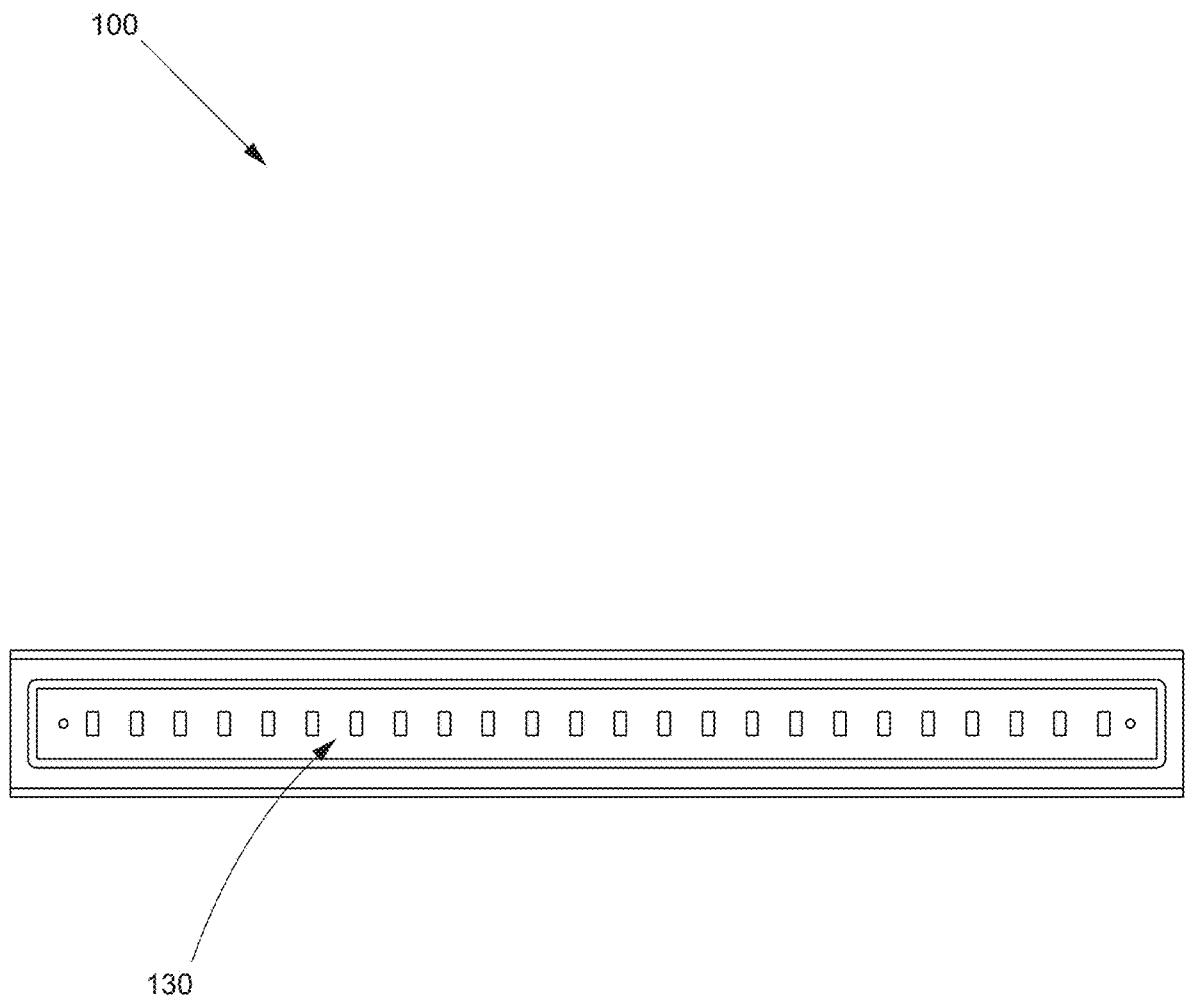
FIG. 3 is front elevation view of an exemplary magnetically attachable UV LED sanitizer in accordance with an embodiment of the invention.

FIG. 3 is front elevation view of an exemplary magnetically attachable UV LED sanitizer in accordance with an embodiment of the invention. Persons having skill in the art will readily appreciate that the rectangular shape of each unit allows for the convenient placement in air conditioning vents, ducts, registers and on or inside grilles.

The LED ultraviolet lamp board is powered and charged by the power board itself. When there is no connection to an external power source, the battery independently supplies electricity to the power board and the remote control board to supply power to the ultraviolet lamp board and the motion detector. The power board plus the remote control board can remotely control the disinfection device through various wireless networking methods.

In embodiments of the invention, the LED ultraviolet lamp board has quartz glass in front of the lamp board for encapsulation and protection. The ultraviolet light source can transmit through the glass for ultraviolet disinfection. The mainboard bracket in the housing is a fixed LED ultraviolet lamp board and power board plus WIFI board and radar board with a shell silicone pad. It acts to buffer the friction when the magnet is attracted. The battery bracket in the casing is used to fix the internal lithium battery as the aluminum front and rear plugs are used to fix the connection between the mainboard bracket and the socket bracket. The aluminum front and rear patches are used to decorate and protect the aluminum plate front and end plugs.

Figure 4:
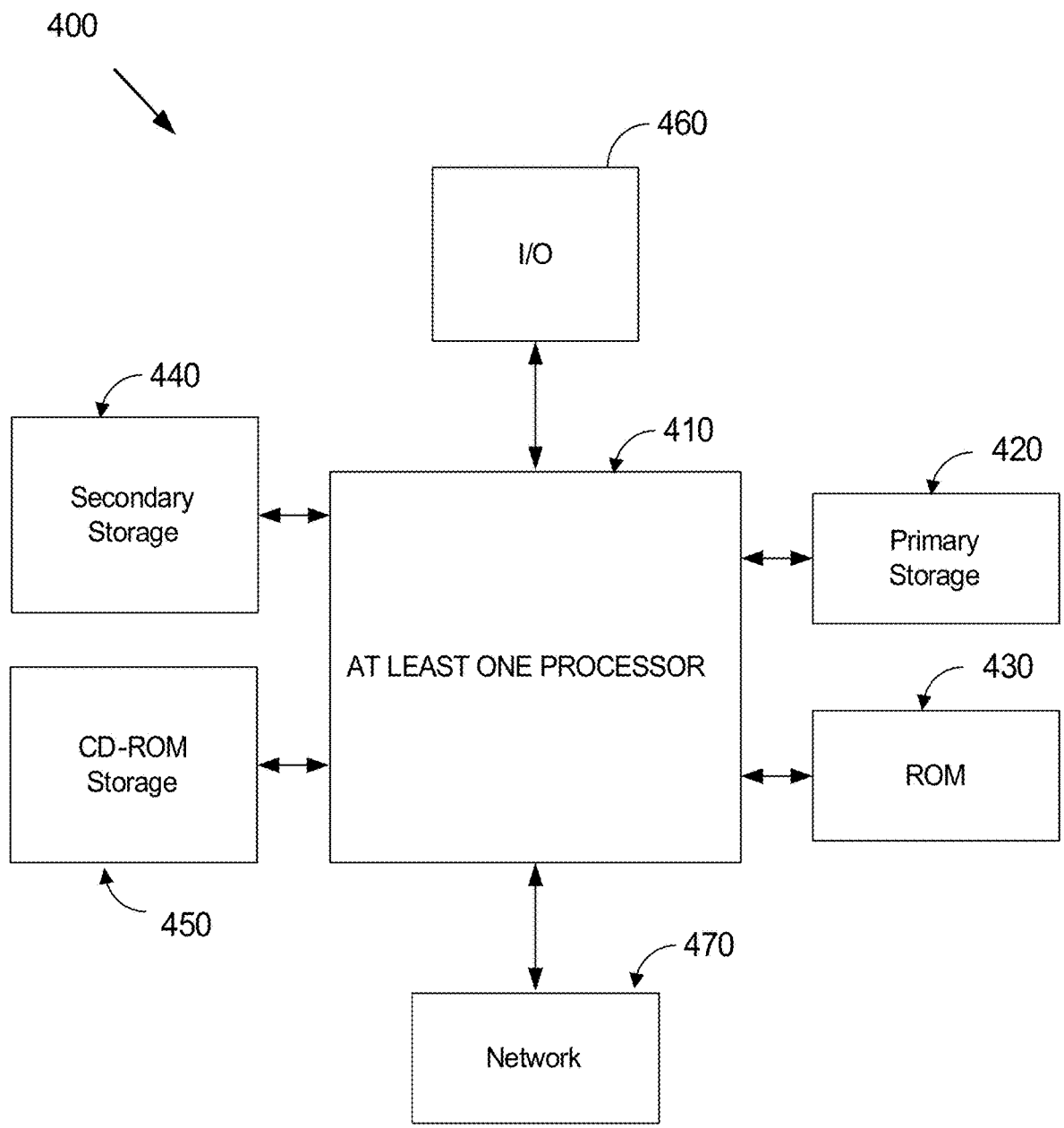
FIG. 4 illustrates a general computer system that, when appropriately configured or designed, can serve as a computer system in which the invention may be embodied.

FIG. 4 illustrates a typical computer system 400 that, when appropriately configured or designed, may serve as a microprocessor board with wireless networking board 220 system for which the magnetically attachable UV LED system, and the components thereof, may be embodied. The computer system 400 includes a quantity of processors 410 (also referred to as central processing units, or CPUs and/or microcontroller units, or MCUs) that may be coupled to storage devices including a primary storage 420 (typically a random-access memory, or RAM), a primary storage 430 (typically a read-only memory, or ROM). The CPU 410 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. As is well known in the art, primary storage 420 acts to transfer data and instructions uni-directionally to the CPU and primary storage 430 typically may be used to transfer data and instructions in a bi-directional manner. The primary storage devices discussed previously may include any suitable computer-readable media such as those described above. A mass storage device 440 may also be coupled bi-directionally to CPU 410 and provides additional data storage capacity and may include any of the computer-readable media described above. Mass storage device 440 may be used to store programs, data and the like and typically may be used as a secondary storage medium such as a hard disk. It will be appreciated that the information retained within mass storage device 440, may, in appropriate cases, be incorporated in standard fashion as part of primary storage 420 as virtual memory. A specific mass storage device such as a CD-ROM 450 may also pass data uni-directionally to the CPU. It will be further appreciated by persons having skill in the art that memory storing computer readable instructions that, when executed by the at least one processor, cause the automated till register system by at least one processor cause the operation of the LED lamp board.

CPU 410 may also be coupled to an interface 460 that connects to one or switches or other well-known input devices such as mice, keyboards, touchpads and even other computers. Finally, CPU 410 optionally may be coupled to an external device such as a database or a computer or telecommunications or internet network using an external connection shown generally as a network 470, which may be implemented as a hardwired or wireless communications link using suitable conventional technologies. With such a connection, the CPU might receive information from the network, or might output information to the network in the course of performing the method steps described in the teachings of the present invention. Persons having skill in the art will understand that the LED lamp board 130 is coupled to such an interface.

Figure 5:
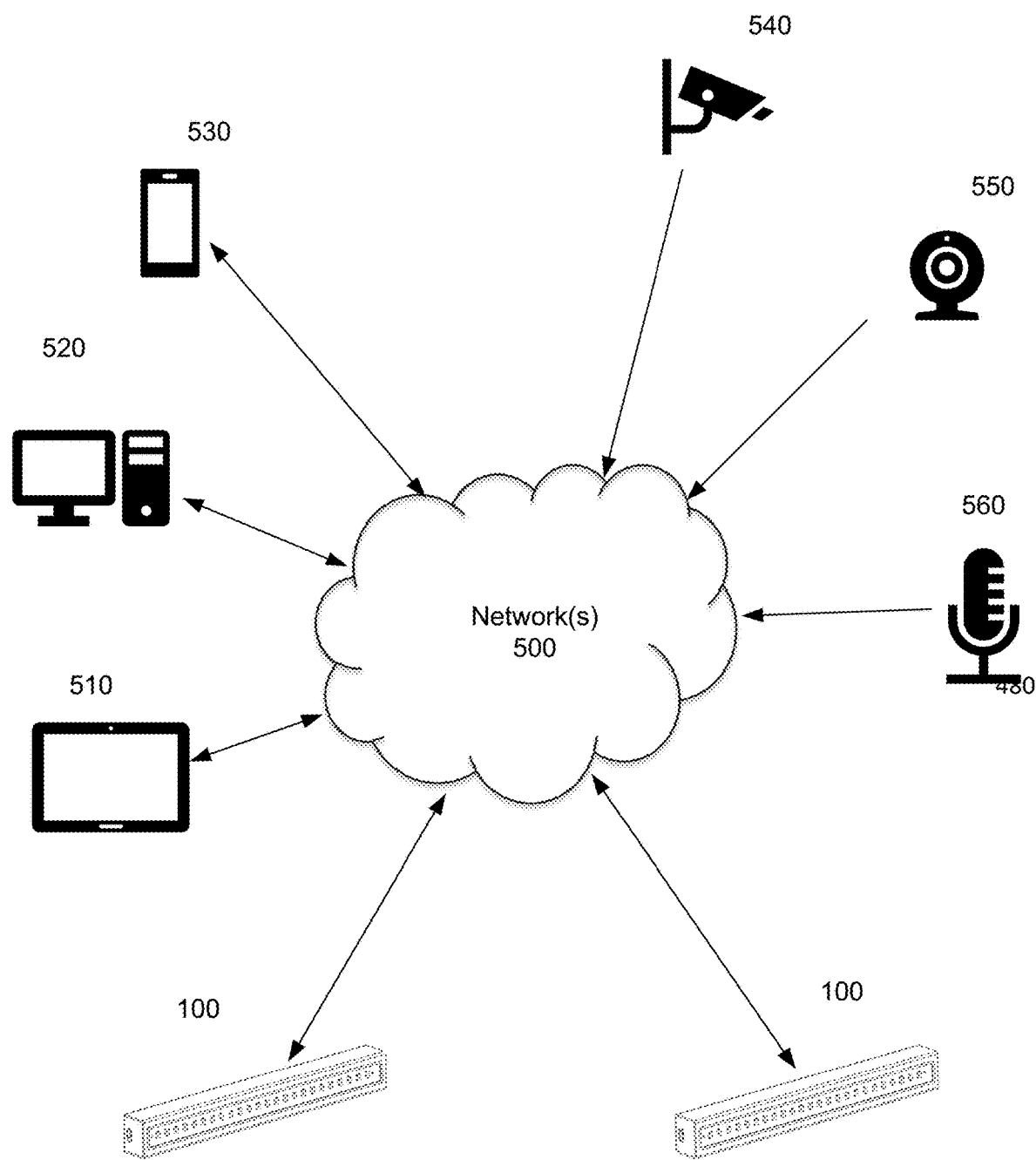
FIG. 5 illustrates a general network diagram to which the magnetically attachable UV LED sanitizer system may be successfully implemented.

FIG. 5 illustrates a general network diagram to which the magnetically attachable UV LED sanitizer system may be successfully implemented. In one embodiment, the network 500 may operate as the Internet or the World Wide Web (WWW). It will be understood by those skilled in the art, though, that communication with the network may take many different forms. Non-limiting examples of forms for communication system include local area networks (LANs), wide area networks (WANs), wired telephone networks, wireless networks, or any other network supporting data communication between respective entities. In the preferred embodiment of the invention, the magnetically attachable UV LED sanitizer system connects to the network through IEEE 802.11 wireless local area network protocols commonly referred to as Wi-Fi. A network may include servers which are capable of providing software or firmware instructions to each magnetically attachable UV LED sanitizer unit as needed.

In embodiments of the invention, the exemplary magnetically attachable UV LED sanitizer unit is networkable with tablets 510, desktop computers and servers 520, and smartphones 530. It will be understood by persons having skill in the art that the each exemplary magnetically attachable UV LED sanitizer unit 100 can network with other magnetically attachable UV LED sanitizer units 100 over the network 500. Furthermore, persons having skill in the art will appreciate that the exemplary magnetically attachable UV LED sanitizer system can be configured to network with devices such as, but not limited to, security cameras 540, web cameras 550 and microphones 560. Persons having skill in the art will readily appreciate that software applications can be developed and implemented on computer platforms ranging from, but not limited to, tablets, smartphones, desktop, laptop and server systems to operate a magnetically attachable UV LED sanitizer system over such a network.

Figure 6:
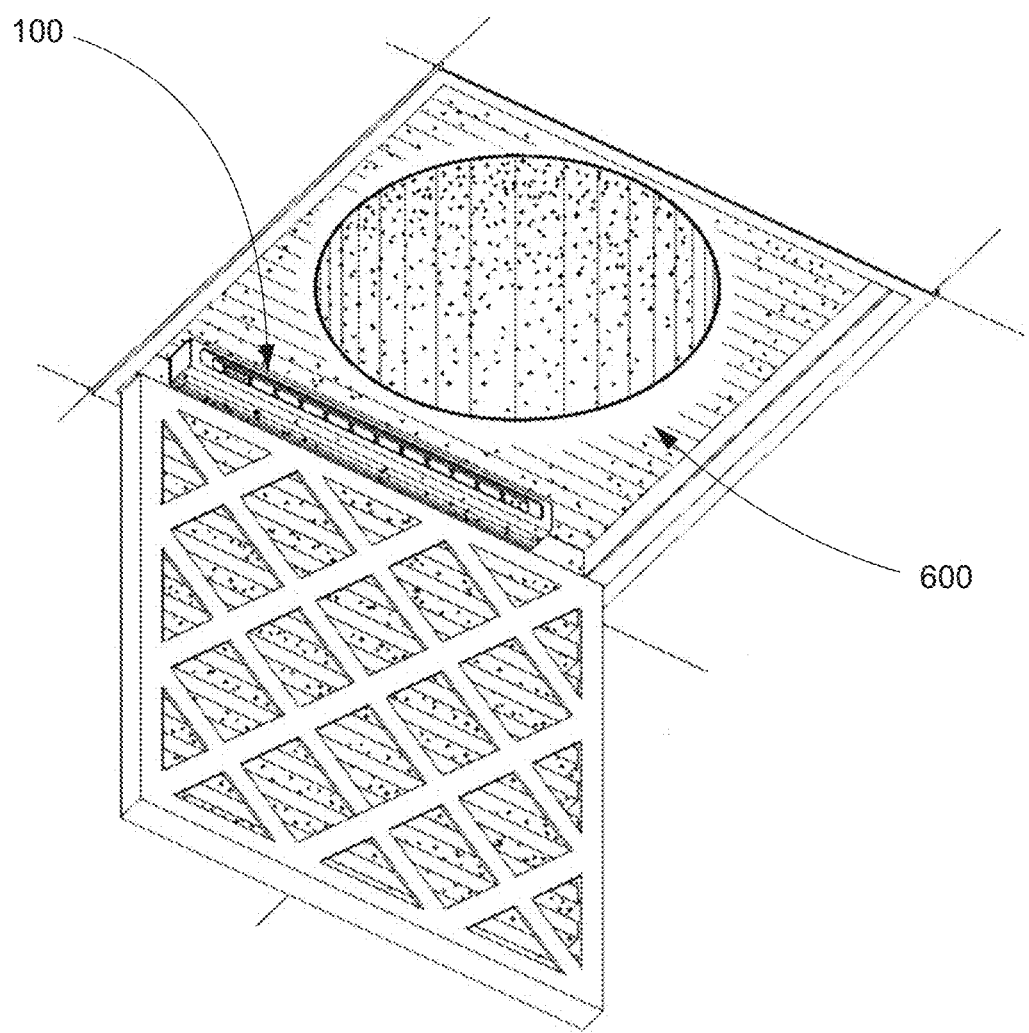
FIG. 6 illustrates a magnetically attachable UV LED sanitizer unit attached to and fitting in an air conditioning register.

FIG. 6 illustrates a magnetically attachable UV LED sanitizer unit 100 attached to and fitting in an air conditioning register 600. Persons having skill in the art will appreciate that the magnetically attachable UV LED sanitizer system may operate in a wide variety of air conditioning ducts, vents, grates and registers. As air flows in, though, and from such ducts, vents, grates and registers, the air passes through a field of germicidal ultraviolet radiation. Such radiation is capable of sanitizing particulates, droplets and aerosols in the travelling air providing sanitized air for indoor spaces.

Use of the magnetically attachable UV LED sanitizer system is designed to be simple and efficient. Use of the magnetically UV LED sanitizer system involves a user connecting the one or more magnetically attachable UV LED sanitizer system units to a wireless network, a user affixing the one or more magnetically attachable UV LED sanitizer system units inside an HVAC duct, register, diffuser and/or grille, a user remotely controlling the one or more magnetically attachable UV LED sanitizer system units over a wireless or wired network, and sanitizing air in indoor spaces using one or more of the said magnetically attachable UV LED sanitizer system units to irradiate air passing into, through or from the said HVAC duct, register, diffuser and/or grille. Persons skilled in the art will readily appreciate that each of the UV LED sanitizer system units can be remotely controlled with a tablet, smartphone or other networked device. Persons skilled in the art will further appreciate that the UV LED sanitizer system units can also be controlled by a motion detector capable of detecting movement of persons in an indoor space which, upon detection of motion, sends an electric signal to the at least one processor which can turn the ultraviolet lamp board.

Having fully described at least one embodiment of the magnetically attachable UV LED sanitizer system, other equivalent or alternative methods of implementing such a magnetically attachable UV LED sanitizer according to the present invention will be apparent to those skilled in the art. Various aspects of the invention have been described above by way of illustration, and the specific embodiments disclosed are not intended to limit the invention to the particular forms disclosed. The particular implementation of the magnetically attachable UV LED sanitizer may vary depending upon the particular context or application. By way of example, and not limitation, the system and method for the magnetically attachable UV LED sanitizer described in the foregoing was principally directed to providing sanitized air in home and/or work spaces. However, similar techniques may instead be applied to other instances where sanitary air sanitizers are required, such as other public indoor spaces such as hospitals or schools, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Although specific features of the magnetically attachable UV LED sanitizer are shown in some drawings and not others, persons skilled in the art will understand that this is for convenience. Each feature may be combined with any or all of the other features in accordance with the invention. The words "including," "comprising," "having," and "with" as used herein are to be interpreted broadly and comprehensively, and are not limited to any physical interconnection. Claim elements and flowchart steps herein may have been numbered and/or lettered solely as an aid in readability and understanding. Any such numbering and lettering in itself is not intended to and should not be taken to indicate the ordering of elements and/or steps in the claims to be added at a later date.

Any amendment presented during the prosecution of the application for this patent is not a disclaimer of any claim element presented in the description or claims to be filed. Persons skilled in the art cannot reasonably be expected to draft a claim that would literally encompass each and every equivalent.

What is claimed is:

1. A magnetically attachable UV LED sanitizer system for sanitizing air in indoor spaces comprising:
    a. an outer shell assembly consisting of a rectangular cuboid outer machine shell, a front plate, and a back plate;
    b. a transparent cover, said cover allowing for the transmission of germicidal ultraviolet light frequencies;
    c. an ultraviolet lamp board;
    d. a central processing unit;
    e. memory;
    f. a power supply;
    g. a rechargeable battery;
    h. a wireless network card; and
    i. a magnet assembly, said magnet assembly positioned on the opposite side of the transparent cover so as to attach to ferromagnetic surfaces.

2. The magnetically attachable UV LED sanitizer system of claim 1 wherein the central processing unit is capable of receiving instructions from other networked devices over a wireless network.

3. The magnetically attachable UV LED sanitizer of claim 1 further comprising a motion detector capable of detecting movement of persons in an indoor space which, upon detection of motion, sends an electric signal to the at least one processor which can turn the ultraviolet lamp board.

4. The magnetically attachable UV LED sanitizer system of claim 1 wherein the ultraviolet lamp board consists of a plurality of LED lights configured to emit germicidal ultraviolet radiation capable of sanitizing air in indoor spaces.

5. The magnetically attachable UV LED sanitizer system of claim 1 wherein the ultraviolet lamp board contains an aluminum substrate to facilitate more efficient heat dissipation.

6. The magnetically attachable UV LED sanitizer system of claim 4 wherein the ultraviolet lamp board emits germicidal ultraviolet radiation at an irradiation angle of 120 degrees and the effective irradiation distance is 50 centimeters.

7. The magnetically attachable UV LED sanitizer system of claim 1 wherein the ultraviolet lamp board is controlled by the central processing unit and memory.

8. The magnetically attachable UV LED sanitizer system of claim 1 wherein the rechargeable battery is a lithium ion battery.

9. A magnetically attachable UV LED sanitizer system for sanitizing air in indoor spaces comprising one or more UV LED sanitizer units, each unit comprising:
    a. An outer shell assembly consisting of a rectangular cuboid outer machine shell, a front plate, and a back plate shaped in such a manner so as to fit inside an air conditioning duct, register, diffuser or grille;
    b. A transparent cover, said cover allowing for the transmission of germicidal ultraviolet light frequencies;
    c. An ultraviolet lamp board having an aluminum substrate insulation layer;
    d. at least one processor;
    e. a motion detector capable of detecting movement of persons in an indoor space which, upon detection of motion, sends an electric signal to the at least one processor which can control the operation of the ultraviolet lamp board;
    f. a power supply;
    g. a rechargeable battery;
    h. a wireless network card;
    i. a magnet assembly, said magnet assembly positioned on the opposite side of the transparent cover so as to attach to ferromagnetic surfaces; and
    j. memory storing computer readable instructions that, when executed by the at least one processor, cause the magnetically attachable UV LED sanitizer system to irradiate a space with germicidal UV radiation from the said ultraviolet lamp board.

10. The magnetically attachable UV LED sanitizer system of claim 9 wherein the at least one processor is capable of receiving instructions from other networked devices over a wireless network.

11. The magnetically attachable UV LED sanitizer of claim 9 further comprising a motion detector capable of detecting movement of persons in an indoor space which, upon detection of motion, sends an electric signal to the at least one processor which can turn the ultraviolet lamp board.

12. The magnetically attachable UV LED sanitizer system of claim 9 wherein the ultraviolet lamp board contains a plurality of LED lights configured to emit germicidal ultraviolet radiation capable of sanitizing air in indoors spaces.

13. The magnetically attachable UV LED sanitizer system of claim 9 wherein the ultraviolet lamp board emits germicidal ultraviolet radiation at an irradiation angle of 120 degrees and the effective irradiation distance is 50 centimeters.

14. The magnetically attachable UV LED sanitizer system of claim 9 wherein the ultraviolet lamp board is controlled by the at least one processor.

15. The magnetically attachable UV LED sanitizer system of claim 9 wherein the rechargeable battery is a lithium ion battery.

16. A method for sanitizing air in indoor spaces using one or more magnetically attachable UV LED sanitizer system units, each unit comprising an outer shell assembly consisting of a rectangular cuboid outer machine shell, a front plate, and a back plate shaped in such a manner so as to fit inside an air conditioning duct register, diffuser or grille; a transparent cover, said cover allowing for the transmission of germicidal ultraviolet light frequencies; an ultraviolet lamp board; a motion detector capable of detecting movement of persons in an indoor space which, upon detection of motion, sends an electric signal to the at least one processor which can turn the ultraviolet lamp board; at least one processor; a power supply; a rechargeable battery; a wireless network card; a magnet assembly, said magnet assembly positioned on the opposite side of the transparent cover so as to attach to ferromagnetic surfaces; and memory storing computer readable instructions that, when executed by the at least one processor, cause the magnetically attachable UV LED sanitizer system to irradiate a space with germicidal UV radiation from the ultraviolet lamp board; said method comprising the steps of:

a. connecting the one or more magnetically attachable UV LED sanitizer system units to a wireless network;

b. affixing the one or more magnetically attachable UV LED sanitizer system units inside an HVAC duct, register, diffuser and/or grille;

c. remotely controlling the one or more magnetically attachable UV LED sanitizer system units over a network; and d. sanitizing air in indoor spaces using one or more of the said magnetically attachable UV LED sanitizer system units to irradiate air passing into, through or from the said HVAC duct, register, diffuser and/or grille.

17. The method of claim 16 wherein the one or more UV LED sanitizer system units are remotely controlled with a tablet, smartphone or other networked device.

18. The method of claim 16 wherein the one or more UV LED sanitizer system units are controlled by a motion detector capable of detecting movement of persons in an indoor space which, upon detection of motion, sends an electric signal to the at least one processor which can turn the ultraviolet lamp board.

\* \* \* \* \*